(12) United States Patent
Braunheim (10) Patent No.: US 8,148,689 B1
(45) Date of Patent: Apr. 3, 2012

(54) DETECTION OF DISTANT SUBSTANCES

(76) Inventor: Stephen T. Braunheim, Los Angeles, CA (US)

( * ) Notice: Subject to any disclaimer, the term of this patent is extended or adjusted under 35 U.S.C. 154(b) by 420 days.

(21) Appl. No.: 12/508,511

(22) Filed: Jul. 23, 2009

Related U.S. Application Data

(60) Provisional application No. 61/083,496, filed on Jul. 24, 2008.

(51) Int. Cl.
*G01N 5/02* (2006.01)
(52) U.S. Cl. ............................. 250/339.07; 250/339.08
(58) Field of Classification Search . 250/339.06–339.08
See application file for complete search history.

(56) References Cited

U.S. PATENT DOCUMENTS

| | | | |
|---|---|---|---|
| 3,931,521 A | 1/1976 | Cinzori | |
| 3,936,193 A | 2/1976 | Auth | |
| 3,989,938 A | 11/1976 | Auth | |
| 4,004,212 A | 1/1977 | Wortman | |
| 4,453,087 A | 6/1984 | Linick | |
| RE31,941 E | 7/1985 | Auth | |
| 4,562,356 A | 12/1985 | Auth | |
| 4,572,668 A | 2/1986 | Auth | |
| 4,652,755 A * | 3/1987 | Solomon et al. | 250/341.7 |
| 4,671,656 A | 6/1987 | Auth | |
| 4,693,603 A | 9/1987 | Auth | |
| RE32,821 E | 1/1989 | Auth | |
| 4,810,092 A | 3/1989 | Auth | |
| 5,002,394 A | 3/1991 | Auth | |
| 5,364,795 A | 11/1994 | Sausa et al. | |
| 5,728,584 A | 3/1998 | Sausa et al. | |
| 5,793,042 A * | 8/1998 | Quick | 250/339.08 |
| 5,826,214 A | 10/1998 | Lieb et al. | |
| 6,034,365 A | 3/2000 | Levin | |
| 6,185,548 B1 | 2/2001 | Schwartz et al. | |
| 6,464,392 B1 * | 10/2002 | Carrieri et al. | 374/45 |
| 6,587,845 B1 | 7/2003 | Braunheim | |
| 6,636,319 B1 | 10/2003 | Auth et al. | |
| 6,895,801 B1 | 5/2005 | Fine et al. | |
| 6,903,343 B2 | 6/2005 | Amon et al. | |
| 6,922,460 B2 | 7/2005 | Skatter et al. | |

(Continued)

OTHER PUBLICATIONS

Ross J. Harper and Kenneth G. Furton, "Biological Detection of Explosives," Chapter 13 in Counterterrorist Detection Techniques of Explosives, ed. J. Yinon, Elsevier, Netherlands, 2007, pp. 395-431.

(Continued)

*Primary Examiner* — David Porta
*Assistant Examiner* — Casey Bryant
(74) *Attorney, Agent, or Firm* — Knobbe Martens Olson & Bear, LLP (57) ABSTRACT

Disclosed are embodiments of methods and apparatus related to detection of substance(s) at a distance. For example, an apparatus can have a mount structure and an emitter mounted to the mount structure and configured to be trained on a target. The emitter can have a source configured to emit radiation and a mirror configured to direct the radiation toward the target. The apparatus can also have a collector mounted to the mount structure and configured to be trained on the target at the same time the emitter is trained on the target and concentrate collected radiation on a sensor. The apparatus can also have a detection system comprising the sensor and an interferometer configured to produce an interferogram. The processor can be configured to perform a Fourier transform on the interferogram to produce a spectrogram and analyze the spectrogram to determine presence or absence of known substances in or around the target.

22 Claims, 3 Drawing Sheets

U.S. PATENT DOCUMENTS

| | | |
|---|---|---|
| 7,002,681 B1 | 2/2006 | Arrieta et al. |
| 7,110,496 B1 | 9/2006 | Amiton et al. |
| 7,162,285 B2 | 1/2007 | Owens et al. |
| 7,204,125 B2 | 4/2007 | Fine et al. |
| 7,227,466 B2 | 6/2007 | Nelson |
| 7,230,244 B2 | 6/2007 | Trotz et al. |
| 7,231,017 B2 | 6/2007 | Gertsenshteyn et al. |
| 7,277,178 B2 | 10/2007 | Shpantzer et al. |
| 7,298,484 B2 | 11/2007 | Chen et al. |
| 7,336,079 B2 | 2/2008 | Stolarczyk et al. |
| 7,336,765 B1 | 2/2008 | Amiton et al. |
| 7,357,043 B2 | 4/2008 | Cumming et al. |
| 2001/0048077 A1* | 12/2001 | Afanassieva ............ 250/339.08 |
| 2004/0095243 A1 | 5/2004 | Holmes et al. |
| 2004/0155202 A1 | 8/2004 | Poteet et al. |
| 2004/0218714 A1 | 11/2004 | Faust |
| 2005/0064600 A1 | 3/2005 | Clark et al. |
| 2005/0253927 A1 | 11/2005 | Allik et al. |
| 2005/0276443 A1 | 12/2005 | Slamani et al. |
| 2006/0082488 A1 | 4/2006 | Keller, III |
| 2006/0239537 A1 | 10/2006 | Shragai et al. |
| 2006/0266102 A1 | 11/2006 | Tolliver |
| 2007/0035304 A1 | 2/2007 | Stolarczyk et al. |
| 2007/0062256 A1 | 3/2007 | Fine et al. |
| 2007/0258562 A1 | 11/2007 | Dinca et al. |
| 2008/0017806 A1 | 1/2008 | Norris |
| 2008/0079937 A1 | 4/2008 | Goodson, III et al. |
| 2008/0084345 A1 | 4/2008 | Rougas et al. |
| 2008/0099692 A1 | 5/2008 | Poreira et al. |
| 2008/0191137 A1* | 8/2008 | Poteet et al. ............... 250/338.1 |

OTHER PUBLICATIONS

Pushkarsky, M. B. et al., "High-sensitivity detection of TNT," Publications of the National Academy of Sciences of the USA, vol. 103, No. 52, pp. 19630-19634, Dec. 26, 2006.

Kopp, Carlo, "Thermal Imaging Sensors," NCW 101 part 6, Defence Today, Strike Publications, May/Jun. 2006, pp. 52-55.

* cited by examiner

DETECTION OF DISTANT SUBSTANCES

CROSS-REFERENCE TO RELATED APPLICATIONS

This application claims the benefit under 35 U.S.C. §119(e) of U.S. Provisional Patent Application No. 61/083,496, filed Jul. 24, 2008, entitled "DETECTION OF DISTANT SUBSTANCES," the entirety of which is hereby expressly incorporated herein for all that it contains.

BACKGROUND

1. Field

Subject matter disclosed herein relates generally to detection and/or identification of substances. For example, spectroscopic analysis may be performed at a distance using a beam of radiation that passes through and/or reflects off a substance to be measured. Spectroscopic devices are discussed.

2. Description of Related Art

Materials, such as explosives and drugs, can emit substances that are detectable. For example, such substances can include volatile organic compounds that are detectable by their odor. Detection of such substances (e.g., by a canine trained to alert to a particular odor) can be used to determine the presence of the material that emits the substance. Trained canines generally must be relatively close to the material in order to detect the substance (e.g., by sniffing a target suspected of carrying the material).

SUMMARY

Disclosed system embodiments are capable of detecting and/or identifying substances that are located at a distance from the system. Certain such embodiments propagate a beam of radiation (e.g., infrared radiation) toward a distant target that may be carrying material or contraband that emits the substance (e.g., a suspect carrying concealed drugs or explosives). The beam of radiation interacts with the substance and at least a portion of the beam of radiation returns to a sensor (e.g., by reflection from the target or a vapor halo adjacent the target). The sensed radiation is analyzed for the presence of one or more substances. In some embodiments, the sensed radiation is spectroscopically analyzed for a spectral signature of the one or more substances. In some such embodiments, a Fourier Transform Infrared (FTIR) spectrometer is used to perform the spectroscopic analysis. In some embodiments, a neural network is used to identify the spectral signature of the one or more substances. In some embodiments, a processor comprising a plurality of processing channels is used to perform the spectroscopic analysis, with each processing channel configured to detect a particular substance. In some embodiments, a suitable signal (e.g., an alert) is provided by the system if at least one substance of interest is detected.

In some embodiments, an apparatus for detecting substances at a distance is disclosed. The apparatus can have: a mount structure; an emitter mounted to the mount structure and configured to be trained on a target, the emitter comprising a source configured to emit radiation and a mirror configured to direct the radiation toward the target; a collector mounted to the mount structure and configured to be trained on the target at the same time the emitter is trained on the target, the collector configured to collect radiation from the direction of the target and concentrate the collected radiation on a sensor; and a detection system comprising the sensor and a Michelson interferometer configured to produce an interferogram based at least in part on a signal from the sensor in response to the collected radiation, the detection system further configured to perform a Fourier transform on the interferogram to produce a spectrogram and analyze the spectrogram to determine presence or absence of a substance in or around the target.

In some embodiments, a method for detecting substances is disclosed. The method can include the following steps: emitting infrared radiation from a source of infrared radiation; reflecting the infrared radiation from a mirror to provide collimated radiation; propagating the collimated radiation through a vapor halo adjacent a target; illuminating a portion of the target with the collimated radiation; collecting radiation from the illuminated target; focusing the collected radiation on an infrared sensor to generate a signal; processing the signal using an to generate an interferogram; mathematically transforming the interferogram to generate a spectrogram; automatically analyzing the spectrogram, via execution of instructions by a computing device, to indicate presence or absence in the vapor halo adjacent the target of a substance with known spectroscopic properties; and storing results of the analysis in a memory.

In some embodiments, an apparatus for detecting substances at a distance is disclosed. The apparatus can comprising the following: a mount configured to be rotatable in at least one plane; an emitter attached to the mount, the emitter configured to propagate a collimated beam of emitted radiation toward a target; a collector attached to the mount, the collector configured to receive radiation that propagates from the target, at least some of the received radiation comprising radiation that has interacted with the target or a vapor halo adjacent the target in response to the collimated, emitted beam; a Fourier Transform spectrometer operatively associated with the collector, the Fourier Transform spectrometer configured to generate a spectrum based at least in part on the received radiation; and a processor configured to analyze the spectrum to detect a presence of at least one substance near the target.

BRIEF DESCRIPTION OF THE DRAWINGS

The following drawings and the associated descriptions are provided to illustrate embodiments of the present disclosure and do not limit the scope of the claims.

These and other features will now be described with reference to the drawings summarized above. The drawings and the associated descriptions are provided to illustrate embodiments and not to limit the scope of any claim. Throughout the drawings, reference numbers may be reused to indicate correspondence between referenced elements.

DETAILED DESCRIPTION

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. Further, no single feature described herein is required or indispensable for each particular embodiment.

Figure 1:
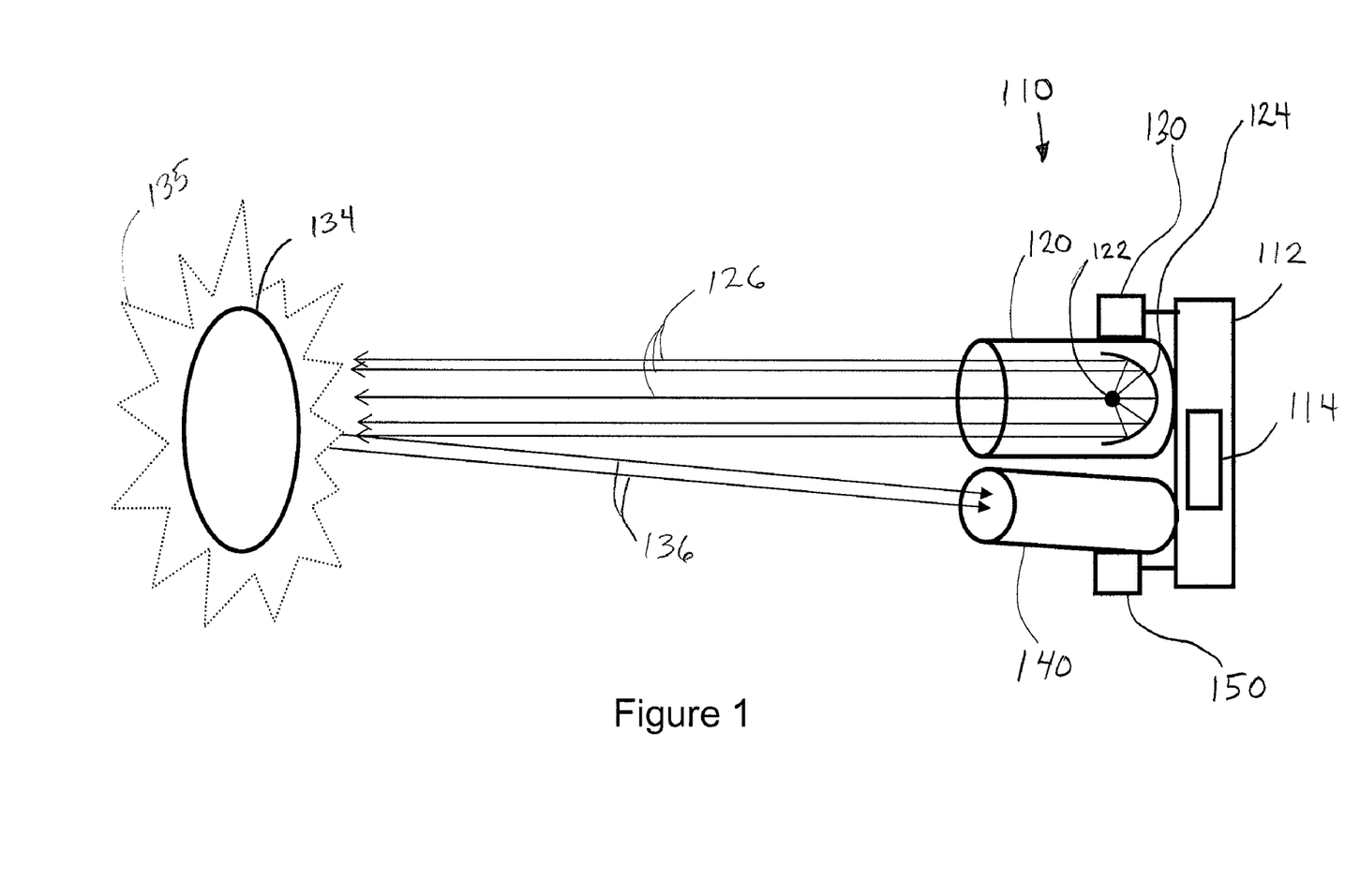
FIG. 1 shows an embodiment of an apparatus for detection of distant substances.

FIG. 1 illustrates an embodiment of a system 110 for detecting substances. The system 110 can comprise a mount structure 112, to which is mounted an emitter 120 and a collector 140. The emitter 120 can comprise a source 122 that radiates emitted radiation 126 that is reflected off a surface of a mirror 124 and directed toward a target 134. The emitter can emit infrared radiation for example. The emitter 120 can have a radiation processor 130 that is mounted thereon as shown or otherwise associated therewith. The mirror 124 can be a parabolic mirror, or can be otherwise shaped in order to cause the emitted radiation 126 to be collimated or conditioned appropriate to the circumstance. The mount structure 112 can be configured to rotate and scan in an angular range (e.g., in a horizontal plane) for example, and can also be configured to rotate in the vertical plane if desired. In some embodiments, the angular range is 360 degrees. In other embodiments, the angular range is 10 degrees, 30 degrees, 45 degrees, 90 degrees, 180 degrees, or some other angular range. The mount structure 112 can have a controller 114 that can be configured to control the physical movement of the mount structure 112 and can also be configured to control a user interface, for example, not shown.

The emitted radiation 126 is directed toward a target 134 that can have a vapor halo 135 surrounding it. The target 134 can be fixed or moving and may be a person, animal, object, building, structure, geological formation or feature, etc. The vapor halo 135 may include one or more substances that are to be detected and/or identified by the system 110. For example, the vapor halo 135 may include substances emitted by explosives, contraband, drugs (e.g., cocaine, cannabis, methamphetamines, etc.), hazardous materials, and so forth that may be carried by, stored in, or otherwise associated with the target 134. The emitted radiation 126 can interact with the target 134 or the general vicinity of the target 134 (e.g., the vapor halo 135). For example, the emitted radiation can be reflected by the target 134 and/or absorbed by the target 134. The emitted radiation 126 can also be reflected, scattered, absorbed, and/or re-radiated (e.g., by fluorescence) by the vapor halo 135.

In some embodiments, the emitted radiation 126 encounters a portion of the vapor halo 135, which causes a diffuse reflection (e.g., backscatter) of the emitted radiation 126, and some of the reflected radiation 136 is directed toward the collector 140. Some of the emitted radiation may pass through the vapor halo 135, reflect off the target 134, and pass a second time through the vapor halo 135 before returning to the collector 140. However, if the emitted radiation 126 is radiation of a particular wavelength that is at least partially absorbed (and/or scattered) by a substance within the vapor halo 135, the reflected radiation 136 may include less energy, intensity, flux, and/or other suitable radiation property than the emitted radiation 126 at the absorbed wave length. The reduced amount of radiation at the absorbed wavelength can be observed by the collector 140, e.g., as a spectral absorption feature. In some cases, the emitted radiation 126 is absorbed and re-radiated by substances in the vapor halo 135. The re-radiated radiation can be observed by the collector 140, e.g., as a spectral emission feature. The properties of the reflected radiation 136 (or re-radiated emission from the vapor halo), as gathered by the collector 140, can be determined by a detection system 150, for example.

In certain embodiments, the controller 114 is configured to control the physical movement of the mount structure 112 so that the emitter 120 tracks or follows a moving target. In some such embodiments, the controller 114 may be configured with tracking algorithms that automatically track a moving target. In some embodiments, the system 110 may be configured with tracking optics (e.g., a tracking scope) such that an operator can manually move the mount structure 112 to track a moving target. In some embodiments, a combination of operator-controlled and automated techniques can be used. Such embodiments of the system 110 can be used to train the emitted radiation 126 on the moving target and to allow the collector 140 to collect the reflected radiation 136 as the target moves relative to the system 110. Certain such embodiments may provide possible advantages. For example, the target 134 may initially be at too great a distance for particular substances to be reliably detected. By tracking the moving target, the system 110 will be able to detect and/or identify the particular substances when the target moves within a suitable range. Also, in some cases, portions of the vapor halo 135 that contain particular substances may be blocked from receiving the emitted radiation 126 (e.g., blocked by the target or a structure behind which the target is hiding). By tracking the target as it moves, the system 110 can detect and/or identify the particular substances when these portions of the vapor halo come into view of the system 110 (e.g., are able to receive the emitted radiation 126).

In one example of a system 110 for detecting substances, the power of the source 122 is about 100 watts, and in some embodiments the power of the source 122 is in the range of about 100 watts to about 1000 watts. For example, 500 watts can be used. Other source powers can be used. In some embodiments, multiple sources 122 can be included. For example, a single lamp may not be able to produce an emitted radiation 126 beam with a temperature much larger than 1300 Kelvin. Thus, an array or set of multiple radiation lamps can be used as the source 122. In some embodiments, a source 122 that is fed with a power of 100 watts can radiate at approximately 1000 Kelvin. A 140 watt lamp can advantageously be used, and, in some embodiments, such a lamp may not radiate in the visible range of wavelengths. A lamp that does not radiate in the visible range has the benefit of being harder to see for humans who may be attempting to see a beam of emitted radiation 126 while a device such as the system 110 is in operation. Thus, a system that is stealthy and/or difficult to detect visually, can have many advantages. In some embodiments, radiation from the source 122 may pass through one or more filters to provide a desired wavelength range for the emitted radiation 126. In some embodiments, various optical elements may be used to process, modify, or redirect the radiation from the source 122 such as, e.g., lenses, mirrors, gratings, dispersive or diffractive elements, modulators, stops, and so forth.

In some embodiments, the mirror 124 can be positioned such that the source 122 is at the focal point of the mirror 124.

For example, the optics of the system 110 can be designed such that the source produces emitted radiation 126 that reflects off the mirror 124 into a collimated beam, much like a search light. In some embodiments, the diameter of the parabolic mirror is 10 inches. In some embodiments, the diameter of the parabolic mirror is 20 inches. The mirror 124 can be gold-plated or coated with a material that is highly reflective to radiation in a wavelength range (e.g., the wavelength range of the emitted radiation 126). In some embodiments, the mirror 124 causes radiation from the source 122 to create an emitted radiation beam 126 that is narrow, collimated, and approximately the size of a pencil. In some embodiments, the narrow, collimated beam has a size that is smaller than the target and/or the vapor halo, about the same size as the target and/or the vapor halo, or larger than the target and/or the vapor halo.

In some embodiments, the mirror 124 (and/or other optical elements) can be configured so that the emitted radiation 126 converges or is focused. For example, in some embodiments, the mirror 124 has a shape that is substantially an ellipse, the source 122 is positioned at a first focus of the ellipse, and the emitted radiation 126 converges at the second focus of the ellipse. Such embodiments advantageously may be used to deliver radiation to a focal point or focal region that may be smaller than the target 134 or the vapor halo 135. Such embodiments may also concentrate the emitted radiation 126 in the focal region, which may, in some cases, cause greater interaction with the substances to be detected, and a larger amount of reflected radiation 136 is returned to the system 110 for analysis.

The radiation processor 130 can be configured to control the intensity, power, wavelength, signal pattern, frequency or wavelength distribution, and/or other parameters of the source 122. The radiation processor 130 can also be configured to control the relative position of the source 122 and the mirror 124, which can be fixed and/or movable, for example. The radiation processor can be configured to detect radiation emitted directly from the source 122 to determine if the source 122 is working properly, for example. The radiation processor 130 can provide input to the controller 114, which can be used to determine the reliability and/or parameters of the emitted radiation 126. The radiation processor 130 can be used to change the emitted radiation 126 by controlling and/or changing a radiation parameter. The radiation parameter can be chosen by a user and a radiation parameter may correspond to a substance (e.g., a chemical in vapor phase) to be detected. In some embodiments, the radiation processor determines the rate at which emitted radiation 126 is periodically (or non-periodically) emitted. For example, the emitted radiation 126 may be pulsed. In some embodiments, the radiation emitted by the emitter 120 is within the infrared portion of the electromagnetic spectrum. For example, the emitter 120 can emit radiation in the approximate range of 8 to 14 micrometers. In some embodiments, the radiation emitted by the emitter 120 corresponds to a temperature that is approximately room temperature (300 Kelvin). In some embodiments, the radiation emitted by the emitter 120 is in the range of 8 to 9 micrometers. In some embodiments, the radiation emitted by the emitter 120 is in the mid-infrared range. In some implementations, the source 122 may emit thermal radiation (e.g., at a temperature in a range from about 300 Kelvin to about 1500 Kelvin). The thermal radiation may be filtered to provide a suitable wavelength range (e.g., about 8 to 14 micrometers) for the emitted radiation 126. Other wavelength ranges can be used including, for example, visible, near-infrared, and/or far-infrared wavelengths. For example, in various embodiments the wavelength range may comprise infrared wavelengths in a range from about 0.8 to 2 micrometers, from about 2 to 14 micrometers, and/or from about 5 to 8 micrometers. In some embodiments, the wavelength range may be selected to include one or more spectral features of interest in the spectrum of a substance. For example, TNT (2,4,6-trinitrotoluene) has strong infrared spectral features at about 6.4 and 7.3 micrometers. The spectral features may include molecular vibrational spectral features of substances of interest (e.g., TNT). In some embodiments, the wavelength range comprises a narrow-band substantially centered around the spectral features (e.g., a band of a few micrometers around one or both of the TNT spectral features).

The collector 140 can be a telescope that is aligned to collect a portion of the emitted radiation 126 that is reflected (and/or scattered) off of the target 134 after having passed through at least a portion of the vapor halo 135. Thus, in some embodiments, the collector 140 and the emitter 120 can be aligned toward the same portion of the target 134 (which can be, for example, approximately the same radius as a common pencil). The collector 140 can comprise a mirror (not shown) that, in some embodiments, can be similar to the mirror 124. For example, a mirror in the collector 140 can be a highly reflective gold-plated mirror. In some embodiments, the diameter of a mirror within the collector 140 can correspond to a diameter of the mirror 124 in the emitter 120. In some embodiments, the collector 140 can comprise a 10 inch F/3 parabolic mirror.

The collector 144 can have a detector (not shown) that can be located at the focal point of a parabolic mirror, in a similar fashion to that illustrated with respect to the source 122 and the mirror 124 in the emitter 120. In some cases, a secondary mirror (not shown) may be used to direct the radiation to a different focal configuration such as, e.g., a Newtonian or Cassegrain focus. The detector (not shown) can be located within the collector 140 (or at an alternative focal configuration). In some embodiments, the detector comprises an infrared detector such as, e.g., a Mercury Cadmium Telluride (MCT) detector. Other detectors can be used such as, e.g., Indium Antimonide detectors, quantum well infrared photodetectors (QWIP), etc. In some embodiments, a multi-element detector array is used. In some embodiments, such a detector can be kept at a low temperature to improve sensitivity. For example, in some embodiments, an MCT detector can be kept at approximately 77 Kelvin (e.g., by cooling with liquid nitrogen). In some embodiments, a Sterling cycle cooler can be used to keep a detector at a low temperature. Other coolers may be used such as, e.g., thermoelectric coolers.

In some embodiments, a detector can be designed to detect multiple wavelengths of radiation. For example, the detector can target a range of electromagnetic radiation that is within a window, to avoid interference from other absorbing molecules that may be in the atmosphere between the system 110 and the target 134. For example, the emitted radiation 126 may pass through water vapor or other substances in the air before the emitted radiation 126 reaches the vapor halo 135 of the target 134. The reflected radiation 136 may also pass through water vapor or other substances on the return path to the collector 140. The detector, by being tuned to a particular range of wavelengths within a window that is not affected by water vapor absorbents (and/or other spectral interferents), can be more highly sensitive to the particular substances within the vapor halo 135, and capable of detecting them without interference. In some embodiments, a detector within the collector 140 can comprise an interferometer that is located at the focal point of a mirror. In some embodiments, the detector is a portion of an interferometer, which can be designed as a Michelson interferometer, a Twyman-Green interferometer, a Fabry-Perot interferometer, or other suitable interferometer, for example. The detector can comprise a Fourier Transform Infrared (FTIR) spectrometer in some embodiments. In some embodiments, the interferometer is operatively associated with the collector 140 and generates a spectrogram of the radiation collected by the collector 140. In some implementations, the interferometer is placed on the ground or a platform (e.g., a table) near the system 110 rather than being attached or mounted to the mount structure 112. Such embodiments may allow the interferometer to operate in a stable, vibration-free environment.

In some embodiments, the detection system 150 can comprise an interferometer, that is operatively associated with the collector 140. In some embodiments, the interferometer can produce an interferogram. In some embodiments, the data produced by the interferometer, and/or detection system 150, can be further processed to produce a spectrogram. For example, the Fourier transform of an interferogram can produce a spectrogram. The processing of an interferogram can be achieved very quickly by taking a Fourier transform, or, a fast Fourier transform, for example. A helium laser can be used to keep the interferometer functioning at a constant rate. For example, the phase of the interferometer is advantageously very regular and precise, and the helium laser advantageously can be used to synchronize the phase of the interferometer. The detection system 150 can comprise a computer processor that performs a Fourier transform and processes the signal from the collector 140 in other ways, such as through noise processing, electrical filtering, bandpass filtering, etc. The computer processor may comprise one or more general or special purpose computers, application specific integrate circuits, field programmable gate arrays, programmable logic devices, etc. In some embodiments, the signal is communicated to a physically remote computer processor for processing.

A spectrometer can be used in place of the interferometer, however, the interferometer can often achieve a result much faster than a spectrometer. However, a spectrometer can be used to achieve a more accurate result in some implementations. For example, the collector 140 and/or detection system 150 can scan at approximately 10,000 cycles per second (Hz). The detection system can scan at other rates such as 10 Hz, 100 Hz, 1000 Hz, etc. The detection system 150, which can comprise a Michelson interferometer, can comprise a spinning mirror that can be used to split the beam of incoming radiation. The helium laser can be used to control and/or improve the timing of the spinning mirror. In some embodiments, use of an interferometer and a processor that takes the Fourier transform of an interferogram, can achieve a useful output at a rate that is 50 times faster than a spectrometer. In some embodiments, the processing of the incoming reflected radiation 136 can be the slowest portion of the process of detecting a substance by the system 110. In some embodiments, the detection system can search a library of data to determine the nature of the substances that are within the vapor halo 135 and/or on the target 134. The detection system 150 can have access to a computer memory that stores data relating to known substances. The data can comprise spectral data relating to the behavior of molecules when those molecules are exposed to radiation within the range of the emitted radiation 126. The data can be obtained from academic chemical studies, and/or from prior use of the system 110 to calibrate with known substances.

In some embodiments, the detection system 150 can comprise a Fourier transform signal that is transmitted to a processor comprising a bus. The bus can communicate with multiple channels, each channel comprising at least one processor. In some embodiments, a channel can be dedicated to the detection of a particular substance and store data relating to that substance and an algorithm for determining whether that substance is present. Thus, a Fourier transform signal can be conveyed to the bus, which in turn conveys the same Fourier transform signal to each of multiple channels, each of which returns a signal to the detection system 150 and/or a user interface (not shown) that indicates an answer pertaining to the presence or absence of particular substances. For example, the answer may be a "yes or no" answer, a likelihood of positive detection, or some other suitable metric that indicates the presence of the substance. In some embodiments, the bus can have a plurality of channels. For example, in some embodiments, 12 channels are implemented, and each of the 12 channels can (but need not) be dedicated to a particular substance. A different number of channels can be used in other embodiments such as, e.g., 1, 2, 3, 4, 5, 8, 10, 20, 30, or more channels. In some embodiments, two or more of the channels may be dedicated to the same substance, which advantageously may improve reliability, accuracy, and/or precision of the detection/identification of the substance. In some implementations, each channel can comprise a portion of a server blade.

The processing algorithms contained within any particular channel (or more than one channel) can comprise a neural network (e.g., a trained neural network, a double neural network, etc.). For example, a double neural network can comport with the principles taught in the Ph.D. thesis of Dr. Benjamin Braunheim. See also, for example, U.S. Pat. No. 6,587,845, entitled "Method And Apparatus For Identification And Optimization Of Bioactive Compounds Using A Neural Network," inventor Benjamin B. Braunheim, issued Jul. 1, 2003, which is hereby incorporated by reference herein in its entirety. A neural network algorithm can provide a fast and accurate result, without requiring a specifically coded algorithm. Thus, in some embodiments, neural network processing algorithms can achieve high speed if the parameters are set to run in a loose enough fashion.

The result from the detection system 150 can be correlated with a result from another detector that may be a part of the system 110. Although not shown, such a separate detector can comprise a thermal imaging system such as, e.g., a forward looking infrared (FLIR) system. The result from the detection system 150 can be compared with a result from a FLIR system, and the two results can be communicated to a user by means of a controller 114 and/or a user interface (not shown) that can be located on the mount structure 112, for example. If the detection system 150 signals a positive result for a particular substance, and that signal coincides with a positive result from an FLIR system, a warning or alarm can be triggered alerting a user to the presence of that substance.

Embodiments of the system 110 can be designed to detect molecules that are related to explosives. Although many molecules can be used to create explosions, many explosive devices include at least one molecule from a group of accelerants. For example, many explosives include the molecule TNT. Many explosives include the molecule RDX. The molecules DNT (related to TNT) and HMX (related to RDX) can also be included in explosives. Many molecules such as TNT and RDX have a very high vapor pressure, and are thus likely to become vapor and be emitted to form a portion of the vapor halo 135, if a target 134 is carrying, wearing, or has recently interacted with an explosive substance. Explosives generally have some degree of out-gassing. Explosive molecules generally do not emit radiation without being excited, and such molecules can be excited with a laser beam, for example, but laser beams are generally too small to be used for scanning an area to detect suicide bombers that may be approaching from 100 yards away, for example. Thus, it can be advantageous to emit a pencil-sized beam of infrared radiation (e.g., using an embodiment of the system 110), which can be invisible to the naked eye, that can be scanned in a sweeping motion around an army check point, for example.

The beam of infrared radiation can be directed to people that may be in a crowd standing off a certain distance from the detection system 110. The beam of emitted radiation 126 can be emitted across the distance of approximately 100 yards (for example), to illuminate people who may be suspected of being carrying explosives (e.g., suicide bombers). If an explosive molecule from the small group of accelerants is present in a vapor halo 135 around a person, the detection system 110 can alert a user to that fact. Various substances can be programmed into a system for detection in this manner. The substances that dogs can be trained to detect can be the substances programmed into the system 110, and in particular programmed into the detection system 150. The explosive materials can be referred to as accelerants and/or oxidants and can include, in addition to TNT or DNT and RDX or HMX, plastic explosives, SEMTEX, nitroglycerine, TAP, etc. Other substances that are candidates for detection can be found in, for example, R. J. Harper and K. G. Furton, "Biological Detection of Explosives" in "Counterterrorist Detection Techniques of Explosives," Jehuda Yinon, editor, Elsevier (Amsterdam) 2007, pp. 395-432, which is hereby incorporated by reference herein in its entirety.

In various implementations, embodiments of the system 110 can be configured to detect and/or identify organic explosives from one or more explosive classes including nitroaliphatics, nitroaromatics, nitrate esters, nitramines, and peroxides. For example, substances that can be detected by embodiments of the system 110 include, but are not limited to: 2,4-dinitrotolune (DNT), 2,4,6-trinitrotolunet (TNT), nitroglycerine (NG), nitrocellulose (NC), pentaerythritol tetranitrate (PETN), trinitro-triazacyclohexane (RDX), tetranitro-tetracyclooctane (HMX), hexanitro-hexaazaisowurzitane (CL20), and triacetone triperoxide (TATP). Diphenylamine, which is commonly present in smokeless powder explosives, can be included. Other substances that can be detected and/or identified include byproducts of the decomposition of explosives (or additives such as plasticizers, stabilizers, and deterrents). Such byproducts can include acetone, hydrogen peroxide, and 2-ethyl-1-hexanol, for example.

Some explosives have relatively low vapor pressure and may not be present in high concentrations in the vapor halo adjacent the target. For such explosives, the system advantageously may be configured to detect and/or identify one or more marker chemicals with much higher vapor pressures that are commonly added to such explosives. Marker chemicals include 2,3-dimethyl-2,3-dinitrobutane (DMNB), 2-nitrotoluene (2-MNT), 4-nitrotoluene (4-MNT), and ethylene glycol dinitrate (EGDN), for example.

In some embodiments, the system 110 is configured to detect and/or identify a set of substances that is representative of a wide range of explosives (or their decomposition byproducts or additives such as, e.g., plasticizers). Although the set of substances may not provide for detection of every possible explosive, the set of substances can be used to detect and/or identify most of the commonly available explosives. For example, in some embodiments, the set of substances can include TNT, DNT, RDX, EGDN, and DMNB.

The system 110 can comprise, and/or be used in conjunction with, a thermal imager. For example, an FLIR thermal imaging system and/or a night vision system can create thermal images of a suspect. The result of thermal imaging can be combined with the result from the system for specific substance detection to create a combined suspect profile. In some embodiments, the combined suspect profile is produced by a single system 110 that may include a thermal imaging capability.

In some applications for an embodiment of the system 110, a terrorist transporting explosives (e.g., a suicide bomber), for example, has not only a chemical signature that indicates the presence of explosive molecules, but the terrorist also has a thermal signature that makes the terrorist a different temperature from the people that surround him or her, or the other background thermal landscape. For example, an explosive belt can cause the terrorist (e.g., a would-be suicide bomber) to appear hotter, or colder, than the surrounding people or objects. Thus, the system 110 can be used to detect and/or verify a suspect of being a potential threat, and the system can achieve such detection across large stand-off distances. For example, the system 110 can be used to detect a terrorist at approximately 100 yards away. In some embodiments, the system 110 can be used to scan a 360° angular range around a military check point, searching for suspected terrorists in a crowd of people.

Embodiments of the system 110 can be used to detect explosives stored or carried in vehicles (e.g., a truck transporting an explosive device), in buildings, in the ground, and so forth. For example, the emitted radiation 126 can be directed toward the vicinity of a suspect vehicle to detect and/or identify explosives in a vapor halo near the vehicle. Many applications of system embodiments are possible.

Various aspects of the system 110 can improve scanning speed. In some implementations, the goal of searching for potential suicide bombers in real time can be achieved using a combination of these principles. For example, as described above, use of a pencil-diameter beam of emitted radiation 126 can improve the system ability to scan a large amount of space and scan more quickly. Moreover, use of Fourier transform and/or fast Fourier transform to process incoming reflected radiation 136 using a detection system 150, can improve speed while maintaining acceptable accuracy. Use of neural network processing principles can also allow fast processing of the resulting signal. In some embodiments, a real-time scan can be achieved if a single pixel is processed each $100^{th}$ of a second. In some embodiments, 16,000 pixels per minute can be processed. In some embodiments, a scan of 360° can be performed in a single minute, allowing a single system 110 to continuously scan a full circumference around a check point, for example, within the time it would require for a potential suicide bomber to run or walk the distance between the bomber and the check point. Another aspect of the system 110 that can improve speed is providing separate processor channels within a detection system 150 for each of a limited number of known explosive substances. Limitation of the processing within the detection system to a certain number of known substances can also improve speed (e.g., a set of substances representative of the majority of available explosives).

Figure 2:
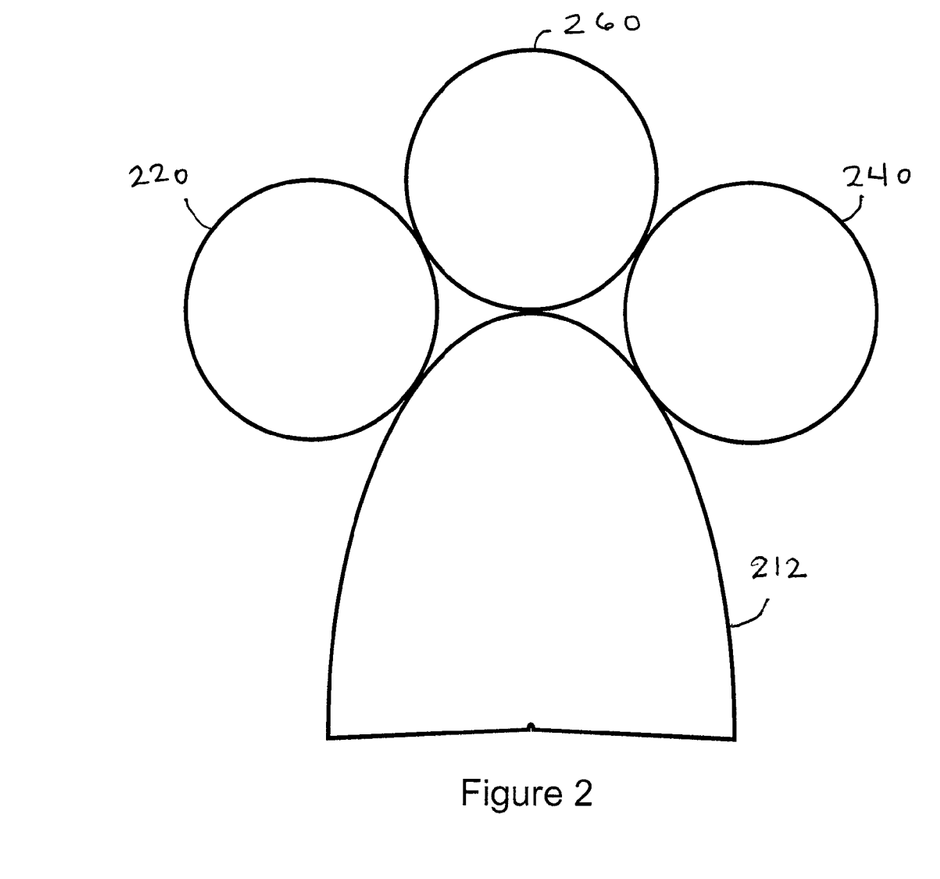
FIG. 2 shows an embodiment of an apparatus for detection and thermal observation of distant substances.

As illustrated in FIG. 2, in some embodiments, a scanning head structure 212 can include both an emitter 220 and a collector 240, as well as a FLIR system 260. FIG. 2 provides a schematic view of the profile of such a combined apparatus, as it may be seen from the perspective of a suspect upon which the instruments 220, 240, and 260 are trained. The FLIR system 260 can scan in multiple spectral regions (e.g., near-infrared, medium-wave infrared, and/or long-wave infrared). The use of an FLIR system with the emitter 220 and collector 240 (along with other components of the system 110, for example) can improve safety at a military check point by providing more information upon which to base defensive and offensive decisions. For example, if the FLIR system indicates that a suspect has a starkly different temperature from its surroundings and the collector 240 and its processor indicate that the presence of an explosive substance in vapor on or around the suspect, the suspect can be even more carefully observed and/or incapacitated.

Figure 3:
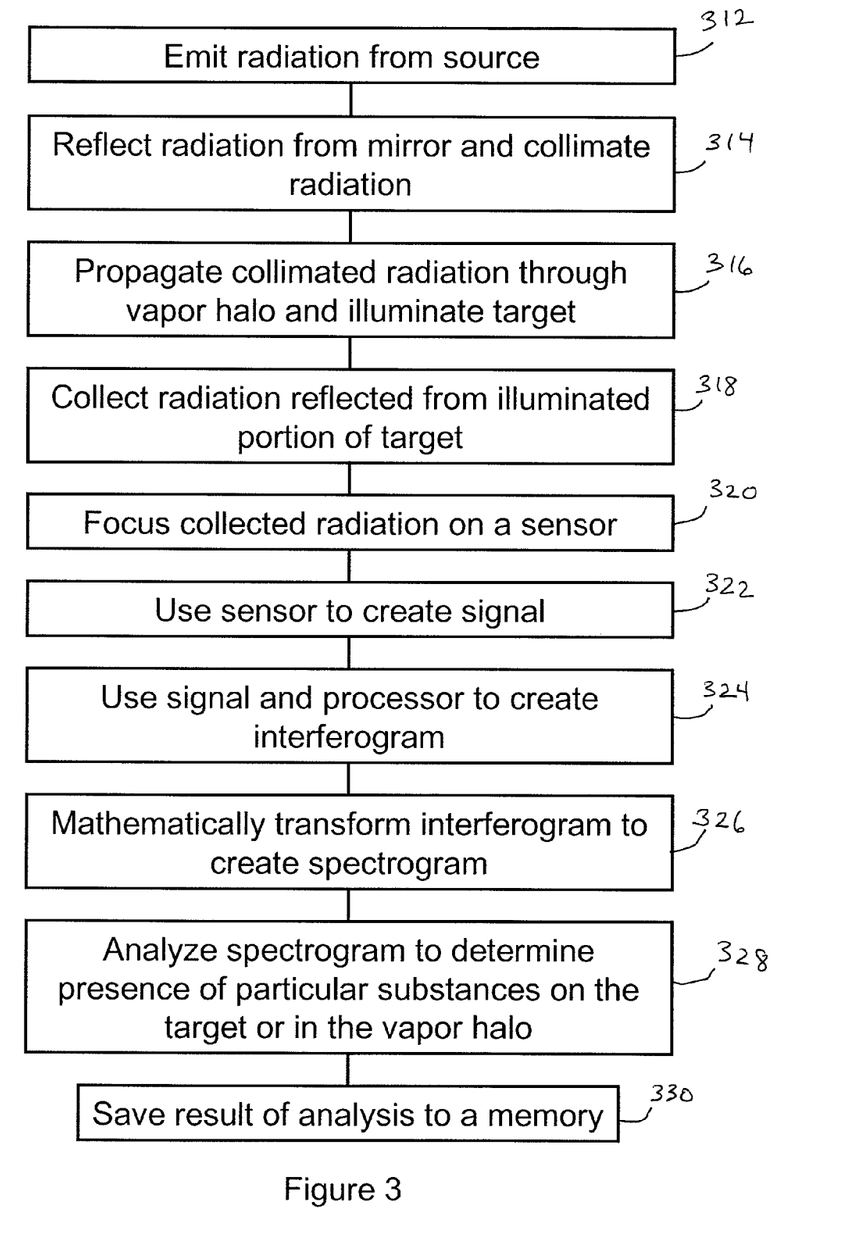
FIG. 3 illustrates steps of an example method for detecting a substance.

In some embodiments, a system for detecting substances can operate or be operated according to the example method illustrated in FIG. 3. In some implementations, an embodiment of the system 110 performs an embodiment of the method illustrated in FIG. 3. For example, radiation (e.g., infrared radiation) can be emitted from a source (or array of sources), as shown at 312. Radiation can be reflected from a mirror (e.g., a gold-coated parabolic mirror) and collimated, as shown at 314. The radiation can be propagated through a vapor halo (e.g., a vapor halo of vaporized explosive components) and illuminate a portion of a target, as shown at 316. Reflected radiation can be collected from the illuminated target or portion of a target (e.g., with a telescope), as shown at 318. Collected radiation can be focused (e.g., with a gold-coated parabolic mirror) on a sensor (e.g., a cooled MCT sensor), as shown at 320. The sensor can create a signal, as shown at 322. The signal can be processed using an interferometer (e.g., an FTIR spectrometer or a Michelson interferometer that uses a spinning mirror to split the beam and a helium laser to keep time) to create an interferogram, as shown at 324. The interferogram can be mathematically transformed (e.g., by taking the Fourier transform or the fast Fourier transform) to create a spectrogram, as shown at 326. The spectrogram can be analyzed automatically (e.g., by using a processor with multiple channels, each channel configured to use neural network methods to indicate presence or absence of a substance with known properties in the vapors or other substances encountered by the radiation), as shown at 328. The result of the analysis can be saved in a memory (e.g. recorded in a computer memory or displayed to a user interface), as shown at 330. The result of the analysis can be stored in a database, communicated via a network (e.g., the Internet) to a suspect tracking website, military command, and so forth.

In various embodiments, some or all of the method, e.g., the mathematical transformation shown at 326 and/or the analysis of the spectrogram shown at 328, may be performed via execution of instructions by a computing device (e.g., one or more general or special purpose computers, processors, ASICs, FPGAs, etc.). Some or all of the computing device may be local and/or remote from the system 110 and in communication with the system 110 via a computer network (e.g., LAN, WAN, Internet). Executable instructions for performing some or all of the method may be stored on a computer-readable storage medium including, but not limited to, magnetic storage media (e.g., RAM, ROM, hard drive), optical storage media (e.g., CD-ROM, DVD), semiconductor storage media (e.g., Flash drive), and so forth.

If the presence of a particular substance is detected, the system 110 may provide a suitable alert or take a suitable action. For example, a warning sound or light may be actuated, a user interface may display information about the detected substance (e.g., on a monitor or display), an electronic message may be communicated (e.g., an e-mail, text message, or the like can be sent to suitable authorities), a warning or other shot may be fired, etc.

Reference throughout this specification to "some embodiments" or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics can be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Embodiments of the disclosed systems and methods can be used and/or implemented with local and/or remote devices, components, and/or modules. The term "remote" may include devices, components, and/or modules not stored locally, for example, not accessible via a local bus. Thus, a remote device may include a device which is physically located in the same room and connected via a device such as a switch or a local area network. In other situations, a remote device may also be located in a separate geographic area, such as, for example, in a different location, building, city, country, and so forth.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may be comprised of connected logic units, such as gates and flip-flops, and/or may be comprised of programmable units, such as programmable gate arrays, application specific integrated circuits, and/or processors. The modules described herein are preferably implemented as software modules, but may be represented in hardware and/or firmware. Moreover, although in some embodiments a module may be separately compiled, in some embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with patients, health care practitioners, administrators, other systems, components, programs, and so forth.

A number of applications, publications, and external documents may be incorporated by reference herein. Any conflict or contradiction between a statement in the body text of this specification and a statement in any of the incorporated documents is to be resolved in favor of the statement in the body text.

Although described in the illustrative context of certain preferred embodiments and examples, it will be understood by those skilled in the art that the disclosure extends beyond the specifically described embodiments to other alternative embodiments and/or uses and obvious modifications and equivalents. Thus, it is intended that the scope of the claims which follow should not be limited by the particular embodiments described above.

What is claimed is:

1. An apparatus for detecting substances at a distance, the apparatus comprising:
   a mount structure;
   an emitter mounted to the mount structure and configured to be substantially collimated to illuminate on a target located at an unknown distance from the emitter, the emitter comprising a source configured to emit radiation and a mirror configured to direct the radiation toward targets located more than 10 yards from the emitter;
   a collector mounted to the mount structure and configured to be trained on the target at the same time the emitter illuminates the target, the collector configured to collect radiation from the direction of the target and concentrate the collected radiation on a sensor, the collected radiation comprising radiation reflected by the target as modified by interactions with any vapor adjacent the target;
   a detection system located on the same side of the target as the emitter and collector, the detection system comprising the sensor and a Michelson interferometer configured to produce an interferogram based at least in part on a signal from the sensor in response to the collected radiation, the detection system further configured to perform a Fourier transform on the interferogram to produce a spectrogram and analyze the spectrogram to determine presence or absence of a substance or plurality of substances in or around the target;
   wherein the emitter, collector, and detection system are grouped together on the same side of the target and thereby form a reflection-based analysis system configured to direct radiation toward—and collect reflected radiation from—targets located more than 10 yards from the emitter, thereby allowing the apparatus to detect a substance at or within vapor adjacent to the distant target without placing any equipment on the far side of the target from the reflection-based analysis system.

2. The apparatus of claim 1, wherein the mirror comprises a gold-coated parabolic mirror.

3. The apparatus of claim 1, wherein the sensor comprises at least one Mercury Cadmium Telluride sensor.

4. The apparatus of claim 1, wherein the detection system is further configured to use a neural network to analyze the spectrogram to determine presence or absence of substances in or around the target.

5. The apparatus of claim 1, wherein the detection system comprises a plurality of processing channels, with each of the processing channels configured to determine presence or absence of a single substance in or around the target.

6. The apparatus of claim 1, further comprising a thermal imaging system mounted to the mount structure and configured to be trained on the target at the same time the emitter and the collector are trained on the target, and wherein the emitter is configured to emit infrared radiation at a power of at least 100 watts.

7. The apparatus of claim 1, wherein the substance comprises an organic explosive, a byproduct from decomposition of the organic explosive, or an additive to a compound comprising the organic explosive.

8. A method for detecting substances at a stand-off distance, the method comprising:
   emitting infrared radiation from a source of infrared radiation at a power of at least 100 watts;
   reflecting the infrared radiation from a mirror to provide collimated radiation that remains substantially collimated for at least 10 yards;
   propagating the collimated radiation for at least 10 yards, through a vapor halo adjacent a target that is located at least 10 yards from the source of infrared radiation;
   illuminating a portion of the target with the collimated radiation;
   collecting reflected radiation from the illuminated target after the radiation has been modified from interaction with the vapor in the vapor halo;
   focusing the collected radiation on an infrared sensor to generate a signal;
   processing the signal using an interferometer to generate an interferogram;
   mathematically transforming the interferogram to generate a spectrogram;
   analyzing the spectrogram, via execution of instructions by a computing device, to indicate presence or absence in the vapor halo adjacent the target of a substance with known spectroscopic properties; and
   storing results of the analysis in a memory.

9. The method of claim 8, wherein collecting radiation from the illuminated target comprises using a telescope to collect radiation that has been reflected by or back-scattered from the illuminated target.

10. The method of claim 8, wherein focusing the collected radiation on a sensor comprises focusing the collected radiation on at least one cooled Mercury Cadmium Telluride sensor.

11. The method of claim 8, wherein processing the signal using an interferometer comprises processing the signal using a Michelson interferometer that uses a helium laser to control the phase of the interferometer.

12. The method of claim 8, wherein mathematically transforming the interferogram comprises taking the Fourier transform of the interferogram to generate the spectrogram.

13. The method of claim 8, wherein automatically analyzing the spectrogram comprises using a neural network to analyze the spectogram.

14. The method of claim 8, wherein the substance comprises an organic explosive, a byproduct from decomposition of the organic explosive, or an additive to a compound comprising the organic explosive.

15. An apparatus for detecting substances at a distance of greater than 10 yards, the apparatus comprising:
   a mount configured to be rotatable in at least one plane;

an emitter attached to the mount, the emitter configured to propagate a collimated beam of emitted radiation at least 10 yards toward a target;

a collector attached to the mount, the collector configured to receive radiation that propagates at least 10 yards from the target, at least some of the received radiation comprising radiation that has interacted with the target or a vapor halo adjacent the target in response to the collimated, emitted beam and then been reflected or scattered back toward the collector;

a Fourier Transform spectrometer operatively associated with the collector, the Fourier Transform spectrometer configured to generate a spectrum based at least in part on the received radiation; and a processor configured to analyze the spectrum to detect a presence of at least one substance near the target.

16. The apparatus of claim 15, wherein the emitted radiation comprises infrared radiation and the Fourier Transform spectrometer comprises a Fourier Transform Infrared spectrometer.

17. The apparatus of claim 15, wherein the at least one substance comprises a first substance and a second substance, and the processor comprises a first processing channel for analyzing the first substance and a second processing channel for analyzing the second substance.

18. The apparatus of claim 15, wherein the at least one substance is selected from the group consisting of nitroaliphatic explosives, nitroaromatic explosives, nitrate ester explosives, nitramine explosives, and peroxide explosives.

19. The apparatus of claim 15, further comprising a scanning system configured to scan the mount in an angular range in the at least one plane.

20. The apparatus of claim 19, wherein the at least one plane comprises a first plane and a second plane, and the scanning system is configured to scan the mount in a first angular range in the first plane and a second angular range in the second plane.

21. The apparatus of claim 15, wherein the emitter is further configured to output at least 100 watts of infrared radiation.

22. The apparatus of claim 15, wherein the emitter is further configured to output radiation for at least 80 yards to the target and the collector is configured to receive radiation that reflects from and propagates back at least 80 yards from the target.

* * * * *

UNITED STATES PATENT AND TRADEMARK OFFICE
CERTIFICATE OF CORRECTION

PATENT NO. : 8,148,689 B1  
APPLICATION NO. : 12/508511  
DATED : April 3, 2012  
INVENTOR(S) : Braunheim, deceased Page 1 of 1

It is certified that error appears in the above-identified patent and that said Letters Patent is hereby corrected as shown below:

On the Title page item [75] at lines 1-2, Change "Stephen T. Braunheim, Los Angeles, CA (US)" to --Stephen T. Braunheim, deceased, Los Angeles, CA (US); Ron R. Goldie, legal representative, Los Angeles, CA (US)--.

In the Specification

In column 7 at line 34, Change "integrate circuits," to --integrated circuits,--.

In column 9 at line 37, Change "2,4-dinitrotolune (DNT)," to --2,4-dinitrotoluene (DNT),--.

In column 9 at line 37, Change "2,4,6-trinitrotolunet (TNT)," to --2,4,6-trinitrotoluene (TNT),--.

In the Claims

In column 13 at line 29, In Claim 1, change "on a" to --a--.

In column 14 at line 60, In Claim 13, change "spectogram." to --spectrogram--.

Signed and Sealed this  
Second Day of July, 2013

Teresa Stanek Rea  
*Acting Director of the United States Patent and Trademark Office*